United States Patent
Brady et al.

(10) Patent No.: US 7,326,246 B2
(45) Date of Patent: Feb. 5, 2008

(54) ACCOMMODATING INTRAOCULAR LENS WITH ELONGATED SUSPENSION STRUCTURE

(75) Inventors: Daniel G. Brady, San Juan Capistrano, CA (US); Arlene Gwon, Newport Beach, CA (US); Robert E. Glick, Lake Forest, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 10/342,125

(22) Filed: Jan. 14, 2003

(65) Prior Publication Data

US 2003/0158599 A1   Aug. 21, 2003

Related U.S. Application Data

(60) Provisional application No. 60/348,708, filed on Jan. 14, 2002.

(51) Int. Cl.
*A61F 2/16* (2006.01)
(52) U.S. Cl. ..................... 623/6.37; 623/6.42
(58) Field of Classification Search ....... 623/6.11–6.55
See application file for complete search history.

(56) References Cited

U.S. PATENT DOCUMENTS

| | | |
|---|---|---|
| 1,483,509 A | 2/1924 | Bugbee |
| 2,129,305 A | 9/1938 | Feinbloom |
| 2,274,142 A | 2/1942 | Houchin |
| 2,405,989 A | 6/1946 | Beach |
| 2,511,517 A | 6/1950 | Spiegel |
| 3,004,470 A | 10/1961 | Ruhle |
| 3,031,927 A | 5/1962 | Wesley |
| 3,034,403 A | 5/1962 | Neefe |
| RE25,286 E | 11/1962 | Decarle |
| 3,210,894 A | 10/1965 | Bentley et al. |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |

(Continued)

FOREIGN PATENT DOCUMENTS

AU            3225789         10/1989

(Continued)

OTHER PUBLICATIONS

Menzo et al. J Cataract Refract. Surg Aug. 24, 1998.

(Continued)

*Primary Examiner*—Bruce Snow
*Assistant Examiner*—Cheryl Miller

(57) ABSTRACT

An intraocular lens (IOL) for insertion in a capsular bag of an eye includes an optic for focusing light and a movement assembly coupled to the optic. The movement assembly is adapted to cooperate with the capsular bag to effect accommodating movement of the optic. The movement assembly includes one or more elongated fixation members coupled to a periphery of the optic and adapted to convert radial movement of the capsular bag to axial movement of the optic. The fixation members extend spirally at least half-way around the optic. Angled transition sections may be provided between each fixation member and the optic periphery. The anterior and posterior edges of the optic periphery may have relatively sharp angles to reduce epithelial cell growth.

4 Claims, 3 Drawing Sheets

U.S. PATENT DOCUMENTS

| | | |
|---|---|---|
| 3,482,906 A | 12/1969 | Volk |
| 3,542,461 A | 11/1970 | Girard et al. |
| 3,693,301 A | 9/1972 | Lemaltre |
| 3,794,414 A | 2/1974 | Wesley |
| 3,922,728 A | 12/1975 | Krasnov |
| 3,932,148 A | 1/1976 | Krewalk, Sr. |
| 4,055,378 A | 10/1977 | Feneberg et al. |
| 4,062,629 A | 12/1977 | Winthrop |
| 4,073,579 A | 2/1978 | Deeg et al. |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,719 A | 12/1980 | Gullino et al. |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A * | 12/1982 | Callahan .................... 623/6.43 |
| 4,370,760 A | 2/1983 | Kelman |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,442,553 A | 4/1984 | Hessburg |
| 4,463,458 A | 8/1984 | Seidner |
| 4,476,591 A | 10/1984 | Arnott |
| 4,504,981 A | 3/1985 | Walman |
| 4,504,982 A | 3/1985 | Burk |
| 4,512,040 A | 4/1985 | McClure |
| 4,551,864 A | 11/1985 | Akhavi |
| 4,560,383 A | 12/1985 | Leiske |
| 4,573,775 A | 3/1986 | Bayshore |
| 4,575,878 A | 3/1986 | Dubroff |
| 4,580,882 A | 4/1986 | Nuchman et al. |
| 4,581,033 A | 4/1986 | Callahan |
| 4,596,578 A | 6/1986 | Kelman |
| 4,617,023 A | 10/1986 | Peyman |
| 4,618,228 A | 10/1986 | Baron et al. |
| 4,618,229 A | 10/1986 | Jacobstein et al. |
| 4,629,460 A | 12/1986 | Dyer |
| 4,636,049 A | 1/1987 | Blaker |
| 4,636,211 A | 1/1987 | Nielsen et al. |
| 4,637,697 A | 1/1987 | Freeman |
| 4,641,934 A | 2/1987 | Freeman |
| 4,676,792 A | 6/1987 | Praeger |
| 4,676,793 A * | 6/1987 | Bechert, II ................ 623/6.54 |
| 4,687,484 A | 8/1987 | Kaplan |
| 4,693,572 A | 9/1987 | Tsnetaki et al. |
| RE32,525 E | 10/1987 | Pannu |
| 4,702,244 A | 10/1987 | Mazzocco |
| 4,704,016 A | 11/1987 | deCarle |
| 4,711,638 A * | 12/1987 | Lindstrom ................ 623/6.54 |
| 4,720,286 A | 1/1988 | Bailey et al. |
| 4,725,278 A | 2/1988 | Shearing |
| 4,752,123 A | 6/1988 | Blaker |
| 4,759,762 A | 7/1988 | Grendahl |
| 4,769,033 A | 9/1988 | Nordan |
| 4,787,903 A | 11/1988 | Grendahl |
| 4,790,847 A | 12/1988 | Woods |
| 4,813,955 A | 3/1989 | Achatz et al. |
| 4,816,032 A | 3/1989 | Hetland |
| 4,830,481 A | 5/1989 | Futhey et al. |
| 4,840,627 A | 6/1989 | Blumenthal |
| 4,842,601 A | 6/1989 | Smith |
| 4,881,804 A | 11/1989 | Cohen |
| 4,888,012 A | 12/1989 | Horn et al. |
| 4,888,014 A * | 12/1989 | Nguyen .................... 623/6.54 |
| 4,888,015 A | 12/1989 | Domino |
| 4,888,016 A | 12/1989 | Langerman |
| 4,890,912 A | 1/1990 | Visser |
| 4,890,913 A | 1/1990 | DeCarle |
| 4,892,543 A | 1/1990 | Turley |
| 4,898,461 A | 2/1990 | Portney |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,932,966 A | 6/1990 | Christie et al. |
| 4,932,968 A | 6/1990 | Caldwell et al. |
| 4,938,583 A | 7/1990 | Miller |
| 4,955,902 A | 9/1990 | Kelman |
| 4,976,534 A | 12/1990 | Milge et al. |
| 4,976,732 A | 12/1990 | Vorosmarthy |
| 4,990,159 A | 2/1991 | Kraff |
| 4,994,082 A | 2/1991 | Richards et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,129,718 A | 7/1992 | Futhey et al. |
| 5,147,397 A | 9/1992 | Christ et al. |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,173,723 A | 12/1992 | Volk |
| 5,192,317 A | 3/1993 | Kalb |
| 5,192,318 A | 3/1993 | Schneider |
| 5,197,981 A * | 3/1993 | Southard ................... 623/6.49 |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,354,335 A | 10/1994 | Lipshitz et al. |
| RE34,998 E | 7/1995 | Langerman |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,521,656 A | 5/1996 | Portney |
| 5,562,731 A | 10/1996 | Cumming |
| 5,574,518 A | 11/1996 | Mercure |
| 5,578,081 A | 11/1996 | McDonald |
| 5,593,436 A | 1/1997 | Langerman |
| 5,607,472 A | 3/1997 | Thompson |
| 5,628,795 A | 5/1997 | Langerman |
| 5,628,796 A | 5/1997 | Suzuki |
| 5,628,797 A | 5/1997 | Richer |
| 5,652,014 A | 7/1997 | Galin et al. |
| 5,652,638 A | 7/1997 | Roffman et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |

| | | | |
|---|---|---|---|
| 5,713,958 A * | 2/1998 | Weiser | 623/6.51 |
| 5,716,403 A * | 2/1998 | Tran et al. | 623/6.46 |
| 5,766,244 A | 6/1998 | Binder | |
| 5,769,890 A | 6/1998 | McDonald | |
| 5,776,191 A | 7/1998 | Mazzocco | |
| 5,814,103 A | 9/1998 | Lipshitz et al. | |
| 5,824,074 A | 10/1998 | Koch | |
| 5,843,188 A | 12/1998 | McDonald | |
| 5,847,802 A | 12/1998 | Meneles et al. | |
| 5,876,442 A | 3/1999 | Lipshitz et al. | |
| 5,898,473 A | 4/1999 | Seidner et al. | |
| 6,013,101 A | 1/2000 | Israel | |
| 6,051,024 A | 4/2000 | Cumming | |
| 6,096,078 A | 8/2000 | McDonald | |
| 6,110,202 A | 8/2000 | Barraquer et al. | |
| 6,162,249 A * | 12/2000 | Deacon et al. | 623/6.16 |
| 6,176,878 B1 | 1/2001 | Gwon et al. | |
| 6,197,058 B1 | 3/2001 | Portney | |
| 6,217,612 B1 | 4/2001 | Woods | |
| 6,231,603 B1 | 5/2001 | Lang et al. | |
| 6,322,589 B1 | 11/2001 | Cumming | |
| 6,342,073 B1 * | 1/2002 | Cumming et al. | 623/6.46 |
| 6,387,126 B1 * | 5/2002 | Cumming | 623/6.37 |
| 6,406,494 B1 | 6/2002 | Laguette et al. | |
| 6,468,306 B1 * | 10/2002 | Paul et al. | 623/6.16 |
| 6,475,240 B1 * | 11/2002 | Paul | 623/6.52 |
| 6,494,911 B2 * | 12/2002 | Cumming | 623/6.37 |
| 6,517,577 B1 * | 2/2003 | Callahan et al. | 623/6.49 |
| 6,533,814 B1 * | 3/2003 | Jansen | 623/6.43 |
| 2005/0246019 A1 * | 11/2005 | Blake et al. | 623/6.46 |
| 2006/0178741 A1 * | 8/2006 | Zadno-Azizi et al. | 623/6.34 |

FOREIGN PATENT DOCUMENTS

| | | |
|---|---|---|
| DE | 2702117 | 7/1978 |
| DE | 3246306 | 6/1984 |
| DE | 4038088 | 6/1992 |
| EP | 0064812 | 11/1982 |
| EP | 0246216 | 11/1987 |
| EP | 0329981 | 8/1989 |
| EP | 0337390 | 10/1989 |
| EP | 0342895 | 11/1989 |
| EP | 0351471 | 1/1990 |
| EP | 0488835 | 6/1992 |
| EP | 0507292 | 10/1992 |
| EP | 0566170 | 10/1993 |
| EP | 0601845 | 6/1994 |
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| WO | 8603961 | 7/1986 |
| WO | 8700299 | 1/1987 |
| WO | 8707496 | 12/1987 |
| WO | 8902251 | 3/1989 |
| WO | 8911672 | 11/1989 |
| WO | 9000889 | 2/1990 |
| WO | 9416648 | 8/1994 |
| WO | 9503783 | 2/1995 |
| WO | 9610968 | 4/1996 |
| WO | 9615734 | 5/1996 |
| WO | 9625126 | 8/1996 |
| WO | 9712272 | 4/1997 |
| WO | 9727825 | 8/1997 |
| WO | 9743984 | 11/1997 |
| WO | 9856315 | 12/1998 |
| WO | 0066039 | 11/2000 |
| WO | 0134067 | 5/2001 |
| ZA | 888414 | 11/1988 |

OTHER PUBLICATIONS

Fechner et al. J Cataract Refract. Surg Jan. 24, 1998.
Amo Specs, Model AC-218, 1992.
Chiron Vision, Nuvita MA20, 1997.
Mandell, Contact Lens Practice, 4$^{th}$ Ed.
Partial Program Re: ASCRS Symposium, Showing Video Tape Shown Between Apr. 10-14, 1999.
Video Tape "New Elliptical Accom. IOL for Cataract Surgery" Shown at ASCRS Symposium on Apr. 10, 1999.
Thornton, Accomodation is Pseudophakia 25, P159.
U.S. Appl. No. 09/390,380, filed Sep. 3, 1999.
U.S. Appl. No. 09/522,326, filed Mar. 9, 2000.
U.S. Appl. No. 09/532,910, filed Mar. 22, 2000.
U.S. Appl. No. 09/565,036, filed May 3, 2000.
U.S. Appl. No. 09/631,223, filed Aug. 2, 2000.
U.S. Appl. No. 09/657,325, filed Sep. 7, 2000.
U.S. Appl. No. 09/656,661, filed Sep. 7, 2000.
U.S. Appl. No. 09/657,251, filed Sep. 7, 2000.
U.S. Appl. No. 09/721,072, filed Nov. 22, 2000.
U.S. Appl. No. 09/795,929, filed Feb. 28, 2001.
U.S. Appl. No. 09/822,040, filed Mar. 30, 2001.

* cited by examiner

ACCOMMODATING INTRAOCULAR LENS WITH ELONGATED SUSPENSION STRUCTURE

RELATED APPLICATION

This application claims the benefit of provisional application Ser. No. 60/348,708, filed Jan. 14, 2002. The disclosure of which is incorporated in its entirety herein by reference.

BACKGROUND OF THE INVENTION

The present invention relates to intraocular lenses (IOLs). More particularly, the present invention relates to IOLs that provide accommodating movement in the eye.

The human visual system includes the eyes, the extraocular muscles which control eye position within the eye socket, the optic and other nerves that connect the eyes to the brain, and particular areas of the brain that are in neural communication with the eyes. Each eye forms an image upon a vast array of light sensitive photoreceptors of the retina. The cornea is the primary refracting surface which admits light through the anterior part of the outer surface of the eye. The iris contains muscles which alter the size of the entrance port of the eye, or pupil. The crystalline lens has a variable shape within the capsular bag, under the indirect control of the ciliary muscle. Having a refractive index higher than the surrounding media, the crystalline lens gives the eye a variable focal length, allowing accommodation to objects at varying distances from the eye.

Much of the remainder of the eye is filled with fluids and materials under pressure which help the eye maintain its shape. For example, the aqueous humor fills the anterior chamber between the cornea and the iris, and the vitreous humor fills the majority of the volume of the eye in the vitreous chamber behind the lens. The crystalline lens is contained within a third chamber of the eye, the posterior chamber, which is positioned between the anterior and vitreous chambers.

The human eye is susceptible to numerous disorders and diseases, a number of which attack the crystalline lens. For example, cataracts mar vision through cloudy or opaque discoloration of the lens of the eye. Cataracts often result in partial or complete blindness. If this is the case, the crystalline lens can be removed and replaced with an intraocular lens, or IOL.

While restoring vision, conventional IOLs have limited ability for accommodation (i.e., the focusing on near objects). This condition is known as presbyopia. To overcome presbyopia of an IOL, a patient may be prescribed eyeglasses. Alternative attempts in the art to overcome presbyopia focus on providing IOLs with accommodation ability. Accommodation may be accomplished by either changing the shape of the IOL, e.g., to become more convex to focus on near objects, or by moving the IOL along its optical axis. Examples of this latter approach are disclosed in Gwon et al. U.S. Pat. No. 6,176,878 and Laguette et al. U.S. Pat. No. 6,406,494.

While many of the prior art approaches provide partial accommodation, a need still exists for an improved IOL configuration that allows sufficient forward axial movement to achieve full-range accommodation.

In view of the foregoing, it would be beneficial in the art to provide IOLs adapted for sufficient accommodation to reduce significantly (or to overcome) the effects of presbyopia.

SUMMARY OF THE INVENTION

The present invention provides new and enhanced intraocular lenses (IOLs) The present IOLs enhance accommodation of an optic. More specifically, the IOLs of the present invention enhance accommodation by converting radial movement of the capsular bag to axial movement of an optic.

In accordance with one aspect of the present invention, an intraocular lens comprises an optic having a circular periphery centered on an optical axis. The optic is adapted to focus light toward a retina of an eye and provide a vision correction. A fixation member attaches to the optic periphery and extends outward therefrom, generally spirally around at least half of the optic. The fixation member desirably extends around at least three-quarters of the optic. The fixation member is longer than previously available, and may have a length of at least about 6 mm.

In one embodiment, there are two of the fixation members symmetrically disposed about a plane through the optical axis. A meridian plane passes through the optical axis and divides the optic into leading and trailing halves. The meridian plane is perpendicular to the direction of insertion of the IOL. A leading one of the fixation members is at least partly located in the leading half of the IOL and attaches to the optic periphery on the meridian plane or in the trailing half.

In a preferred embodiment, the optic and fixation member are integrally formed as a single homogeneous piece. In one version, the fixation member extends outward from the optic periphery and diverges into two beams that are sized to contact the interior of the capsular bag of the eye and provide accommodating movement to the optic. Furthermore, the optic periphery desirably has a relatively sharp posterior edge to prevent epithelial cell growth onto the optic.

In accordance with another aspect of the present invention, an intraocular lens (IOL), comprises an optic having a circular periphery centered on an optical axis. The optic is adapted to focus light toward a retina of an eye and provide a vision correction. A meridian plane passes through the optical axis and divides the IOL into leading and trailing halves. Finally, a pair of fixation members attaches to the optic periphery; a leading fixation member is attached either on the meridian plane or in the trailing half of the IOL, and a trailing fixation member is attached either on the meridian plane or in the leading half of the IOL. Further, the fixation members are both sized to contact the interior of the capsular bag of the eye and adapted to provide accommodating movement to the optic.

The fixation members each preferably extend around at least three-quarters of the optic, and each have a length of at least about 6 mm. Desirably, the optic and fixation members are integrally formed as a single homogeneous piece.

Each fixation member preferably has an inner end adjacent the optic periphery and an outer end configured to contact the interior of the capsular bag of the eye. The outer end of the leading fixation member is in the leading half of the IOL and the outer end of the trailing fixation member is in the trailing half of the IOL.

Each fixation member may have an inner end adjacent the optic periphery and an outer end configured to contact the interior of the capsular bag of the eye, wherein the IOL further includes a transition section interposed between the inner ends of the fixation members and the optic periphery. Each transition section is angled with respect to the optical axis so as to offset the inner ends of each fixation member from an optic plane passing through the center of the optic and perpendicular to the optical axis.

In accordance with a still further aspect of the present invention, an intraocular lens is provided that comprises an optic, a fixation member, and a transition section therebetween. The optic has a circular periphery centered on an optical axis and focuses light toward a retina of an eye and provides a vision correction. The optic further has an anterior face and a posterior face spaced apart on opposite sides of an optic plane perpendicular to the optical axis. The fixation member has an inner end and an outer end. The transition section lies between the fixation member inner end and the optic periphery and has an inner portion connected to the optic periphery and an outer portion connected to the fixation member. The outer portion is displaced along the optical axis with respect to the inner portion in an anterior direction. Furthermore, the fixation member extends generally in a plane parallel to the optic plane but displaced therefrom along the optical axis in the anterior direction.

Preferably, the optic periphery has a relatively sharp posterior edge, and may also have a relatively sharp anterior edge. In one embodiment, there are two of the fixation members and transition sections diametrically opposed across the optic. Moreover, each of the fixation members may extend generally spirally about halfway around the optic.

Each and every feature described herein, and each and every combination of two or more of such features, is included within the scope of the present invention provided that the features included in such a combination are not mutually inconsistent.

Additional aspects, features, and advantages of the present invention are set forth in the following description and claims, particularly when considered in conjunction with the accompanying drawings in which like parts bear like reference numbers.

DESCRIPTION OF THE PREFERRED EMBODIMENTS

Figure 1:
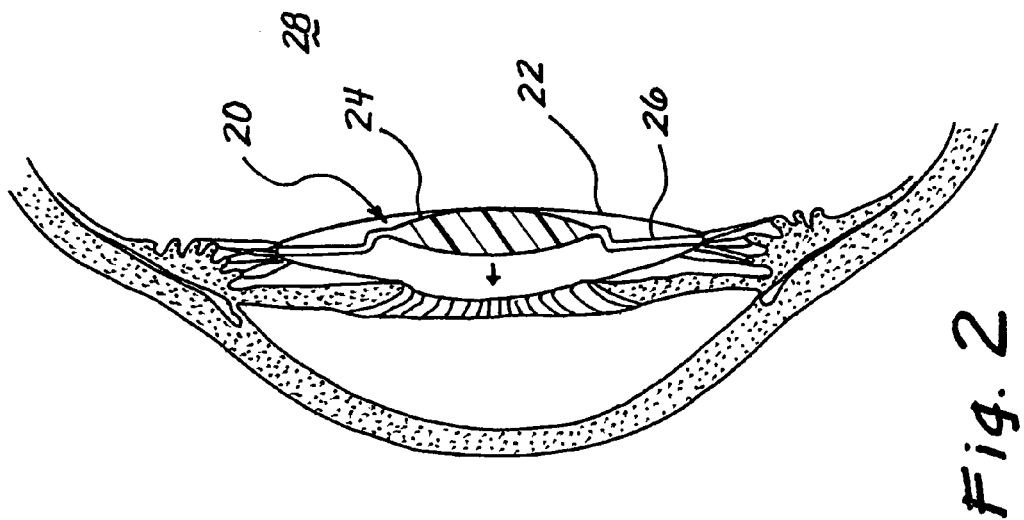
FIG. 1 is a vertical cross-section of an eye illustrating an exemplary intraocular lens of the present invention positioned within the capsular bag.
Figure 2:
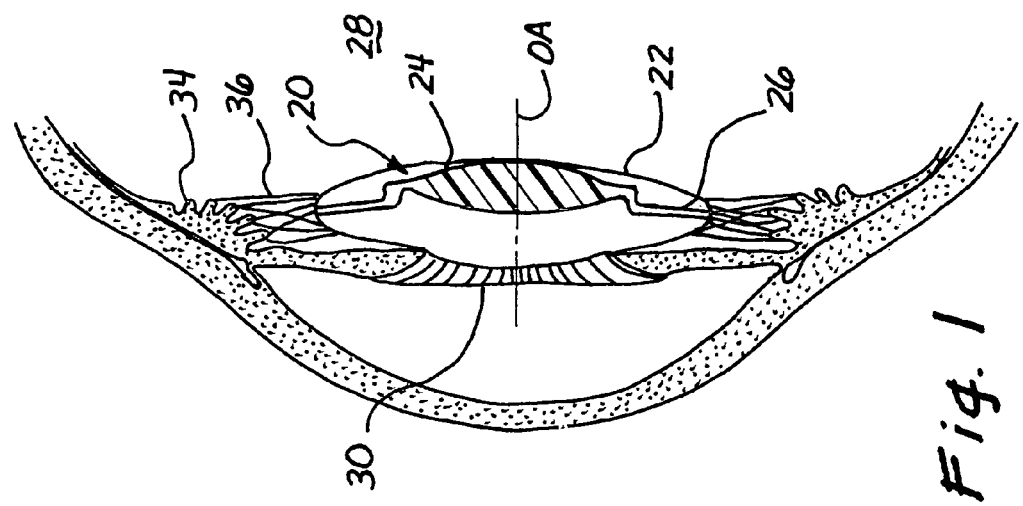
FIG. 2 is a cross-section similar to FIG. 1 showing forward or anterior movement of an optic of the intraocular lens.

Referring to the drawings in more detail, an intraocular lens (IOL) 20 according to an exemplary embodiment of the present invention is illustrated in FIGS. 1 and 2 after implantation in the capsular bag 22 of an eye. Exemplary IOL 20 includes an optic 24 and a movement assembly 26 coupled thereto. The optic 24, which has an optical axis OA, is adapted to focus light onto a retina of an eye. The movement assembly 26 of exemplary IOL 20 cooperates with the eye to effect accommodating movement of the optic 24 and, in particular, converts radial movement (i.e., movement perpendicular to the optical axis OA) of the capsular bag of an eye to axial movement (i.e., movement parallel to the optical axis OA) of the optic 24. In the exemplary embodiment, the movement assembly 26 biases the optic 24 in a posterior direction (to the right) against the posterior wall of the capsular bag 22.

A brief description of the anatomy of the eye is appropriate in order to understand the invention. The capsular bag 22 resides in the posterior chamber of the eye and is in direct contact with the jelly-like vitreous humor 28 which fills the nearly spherical space between the capsular bag and the retina (not shown). In a healthy person, the capsular bag 22 contains the natural crystalline lens which transmits light passing through the orifice of the iris 30 to the retina. The capsular bag 22 is connected to an annular ciliary muscle 34 by suspensory ligaments or zonules 36. The ciliary muscle 34 is the chief agent in accommodation, i.e., in adjusting the eye to focus on near objects. The zonules 36 retain the lens in position and are relaxed by the contraction of the ciliary muscle 34, thereby allowing a natural crystalline lens to become more convex.

Applying this anatomy to the present invention, exemplary IOL 20 is configured to facilitate movement of the optic 24 in response to the action of the ciliary muscle 34 and the zonules 36. When the ciliary muscle 34 constricts inward the zonules 36 relax and reduce the equatorial diameter of the capsular bag 22, wherein the optic 24 translates in the posterior direction against the rear wall of the capsular bag 22. Conversely, when the ciliary muscle 34 relaxes, the zonules 36 tense and increase the equatorial diameter of the capsular bag 22, thereby moving the optic 24 in the anterior direction. In the illustrated embodiment, the optic 24 is biased against the rear wall of the capsular bag 22 at all times, and axial movement of the optic from the action of the ciliary muscle 34 is primarily governed by the position of the rear wall. That is, changes in pressure of the vitreous humor 28 act on the rear wall of the capsular bag 22 and cause it to translate in the axial direction. For example, FIG. 2 illustrates forward movement of the optic 24 from increase in pressure of the vitreous humor 28. One advantage of the present invention is that the optic 24 remains biased against the rear wall of the capsular bag 22 yet can accommodate substantial forward or anterior movement because of long fixation members.

Figure 3:
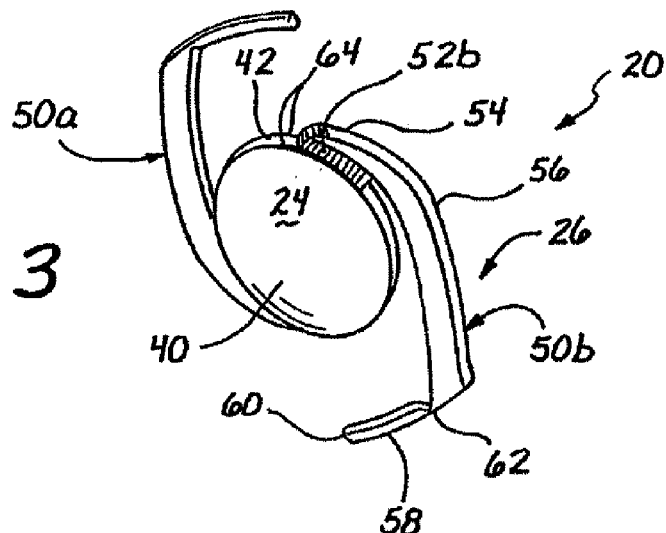
FIG. 3 is a perspective view of the exemplary intraocular lens of the present invention.
Figure 4:
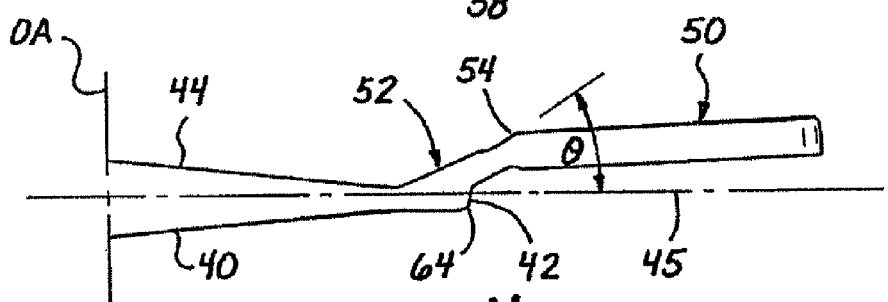
FIG. 4 is a sectional view of one half of the intraocular lens of FIG. 3 taken radially through the optic and then through one of the fixation members.
Figure 5:
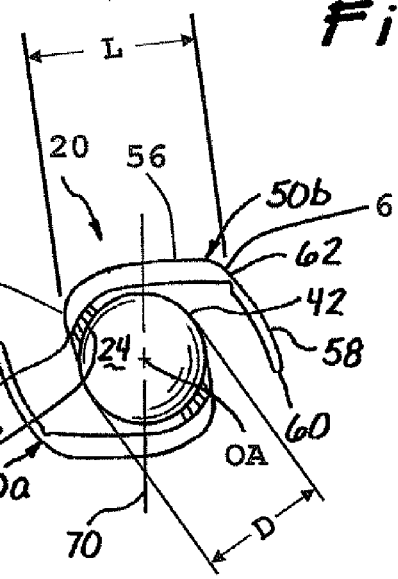
FIG. 5 is a plan view of the exemplary intraocular lens of FIG. 3.

FIGS. 3-5 illustrate the exemplary IOL 20 in perspective, half-section, and plan view, respectively. The posterior aspect of the IOL 20 is seen in FIG. 3 such that a posterior face 40 of the optic 24 faces out of the page. A generally circular periphery or peripheral edge 42 defines the radially outer extent of the optic 24 and separates the posterior face 40 from an anterior face 44 (see FIG. 4). The optic 24 is typically circular, but may exhibit a different shape as long as the optical correction character is centered about the optical axis OA. As seen in FIG. 4, both the posterior face 40 and anterior face 44 are convex such that the optic 24 is considered bi-convex. Of course, those of skill in the art will understand that the anterior and posterior faces can take other shapes, such as planar or concave. In any event, the posterior face 40 and anterior face 44 are spaced apart on opposite sides of an optic plane 45 that extends perpendicular to the optical axis OA. In other words, the optic 24 is centered on and oriented in the optic plane 45.

As best seen in FIGS. 3 and 5, the movement assembly 26 comprises a pair of fixation members 50a, 50b connected to and extending radially outward from the circular periphery 42 of the optic 24. A transition section 52 is interposed between each of the fixation members 50a, 50b and the periphery 42. The transition section 52 can be seen in FIG. 4 and extends at an angle θ in an anterior direction with respect to the optic plane 45. In a preferred embodiment, θ is approximately 15°. Referring to FIG. 5, the transition section 52b is circumferentially disposed about a midpoint 67 and extends alone the peripheral edge 42 of the optic 24.

As seen in FIGS. 3 and 4, each fixation member 50a, 50b has a proximal end 54 connected to the respective transition section 52a, 52b, an accommodating beam 56, and a stabilizing arm 58 terminating in a distal end 60. In the illustrated embodiment shown in FIG. 3, the distal end 60 is free in that each fixation member 50a, 50b is detached from other portions or elements of the IOL 20 at the distal end 60. The accommodating beam 56 is substantially wider in plan view than the stabilizing arm 58 and is connected thereto at a relatively thin living hinge 62. Each fixation member 50a, 50b is desirably oriented in a plane that is spaced from the optic plane by virtue of the angled transition section 52. The fixation members 50a, 50b are desirably co-planar, but may be slightly angled with respect to one another.

Although controlled fibrosis (i.e., cellular growth) on the stabilizing arm 58 may be desirable, the IOLs 20 of the invention inhibit cell growth, particularly epithelial cell growth, onto the optic 24. This is accomplished by configuring the periphery 42 of the optic 24 with mechanical barriers such as relatively sharp posterior and anterior edges 64 shown in FIGS. 3 and 4. The proliferation of unwanted epithelial cell growth may also be inhibited through the use of material properties.

The fixation members 50a, 50b of the IOL 20 are substantially longer than previous fixation members. When there are two fixation members, the surgeon typically identifies them as leading and trailing with reference to their orientation during the implant procedure. The accepted technique is to insert, through the incisions in the cornea and the capsular bag, a first or leading one of the fixation members, then the optic, then the other or trailing fixation member. With respect to FIG. 5, a meridian plane 70 is drawn that divides the IOL 20 into a leading half to the left, and a trailing half to the right. The primary location of the fixation members 50a, 50b on either side of the meridian plane 70 determines whether they are leading or trailing. Therefore, because the fixation member 50a is primarily located on the left of the meridian plane 70, it is considered to be the leading member, while the trailing fixation member is indicated as 50b. Alternatively, the location of the terminal end 60 may signify whether the corresponding fixation member 50 is leading or trailing.

Referring to FIG. 5, the elongate accommodating beam 56 has a length L and is configured to be substantially straight along its length. The elongate accommodating beam 56 and the elongate stabilizing arm 58 are configured to form an obtuse angle when the IOL 20 is in an unstressed state outside the eye. The optic 24 has a diameter D and the length L of the elongate accommodating beam 56 may be selected to be greater than the diameter D of the optic 24.

The increased length of fixation members 50a, 50b may be obtained as illustrated in FIG. 5. For example, the transition section 52b for the top elongate accommodating beam 56 of the fixation member 50b is entirely disposed in the leading half of the meridian plane 70 and a distal end 66 of the elongate accommodation beam 56 is disposed in the trailing half of the meridian plane 70. The elongate accommodating beam 56 is disposed substantially perpendicular to the meridian plane and such that a line through the optical axis OA and the circumferential midpoint 67 forms an acute angle with a line disposed along the length of elongate accommodation beam. A similar arrangement of the fixation members 86a, b is also illustrated in FIG. 6.

The present invention provides long fixation members 50a, 50b by virtue of the leading fixation member 50a attaching to the optic periphery 42 along the meridian plane 70 or in the trailing half. Likewise, the trailing fixation member 50b attaches to the optic periphery 42 along the meridian plane 70 or in the leading half, and is thus longer than previous fixation members. In terms of absolute length, each of fixation members 50a, 50b is at least 6 mm long from its inner end 54 to its outer end 60.

Figure 6:
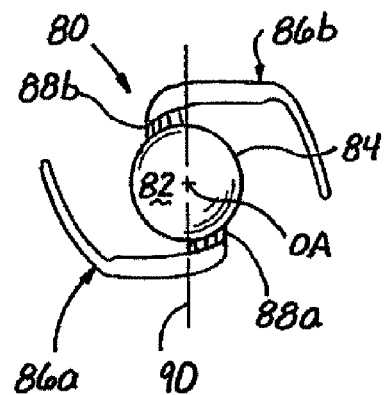
FIG. 6 is a plan view of an alternative intraocular lens of the present invention.

FIG. 6 illustrates an alternative IOL 80 of the present invention that is in many ways similar to the IOL 20 illustrated in FIGS. 3-5. In particular, the IOL 80 has a generally circular optic 82, having a periphery 84 from which a pair of fixation members 86a, 86b extend outward. As in the first embodiment, angled transition sections 88a, 88b locate the fixation members 86a, 86b out of the optic plane (parallel to the page) in the anterior direction.

A meridian plane 90 extending through the optical axis OA divides the IOL 80 into a leading half on the left, and a trailing half on the right. Again, the halves of the IOL are determined by the orientation of the fixation members 86a, 86b during implant, such that the surgeon inserts the fixation member 86a first through the incisions in the eye. As in the earlier embodiment, the fixation members are relatively long. More particularly, the leading fixation member 86a connects to the optic periphery 84 along the meridian plane 90 or in the trailing half. Likewise, the trailing fixation member 86b connects to the optic periphery 84 along the meridian plane 90 or in the leading half. As can be seen by comparing FIGS. 5 and 6, the transition sections 88a, 88b are located closer to the meridian plane 90 in the alternative embodiment than the corresponding elements were in the first embodiment.

Figure 7:
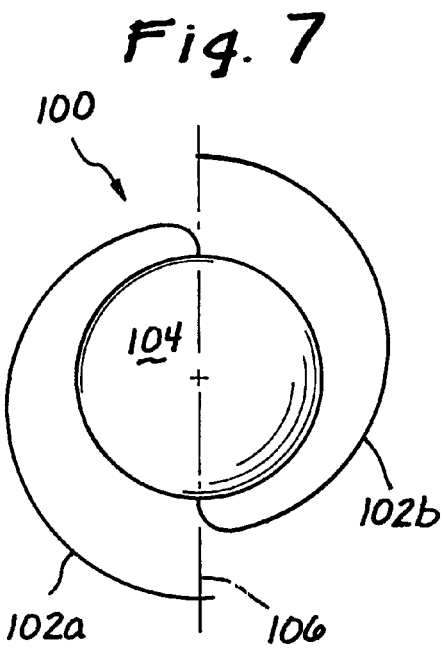
FIGS. 7-9 are schematic plan views of further alternative intraocular lenses of the present invention.
Figure 8:
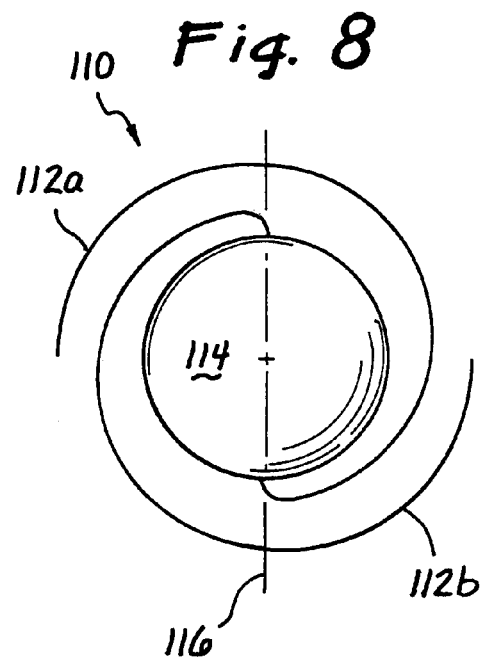
Figure 9:
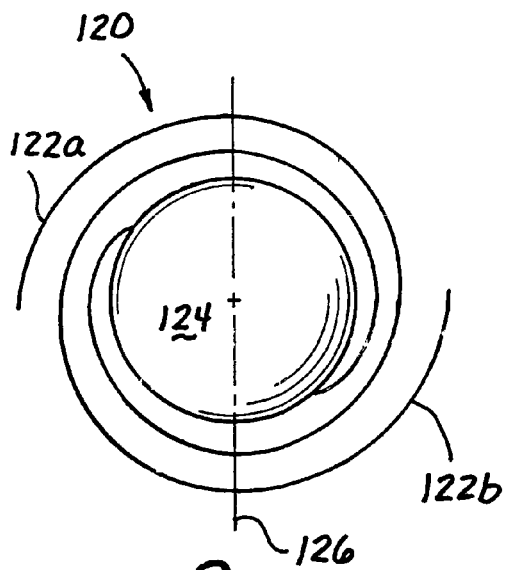

FIGS. 7-9 schematically illustrate intraocular lenses that have two fixation members extending spirally around an optic.

An IOL 100 of FIG. 7 has a leading fixation member 102a and a trailing fixation member 102b, each of which spirally extends around approximately half the circumference of an optic 104. Each fixation member 102 connects to the optic 104 along a meridian plane 106 that divides the IOL 100 into leading (left) and trailing (right) halves. In this orientation, therefore, the IOL 100 is inserted to the left into the eye.

An IOL 110 of FIG. 8 has a leading fixation member 112a and a trailing fixation member 112b, each of which spirally extends around approximately three-quarters of the circumference of an optic 114. Each fixation member 112 connects to the optic 114 along a meridian plane 116 that divides the IOL 110 into leading (left) and trailing (right) halves. In this orientation, therefore, the IOL 110 is inserted to the left into the eye.

An IOL 130 of FIG. 8 has a leading fixation member 112a and a trailing fixation member 112b, each of which spirally extends around approximately three-quarters of the circumference of an optic 114. Each fixation member 112 connects to the optic 114 along a meridian plane 116 that divides the IOL 110 into leading (left) and trailing (right) halves. In this orientation, therefore, the IOL 110 is inserted to the left into the eye.

Although the illustrated embodiments show two fixation members, only one, or three or more, may also be used. In this context, each fixation member is separately connected to the optic. Therefore, if there are multiple strands but only one point of connection, there is only one fixation member.

Figure 10:
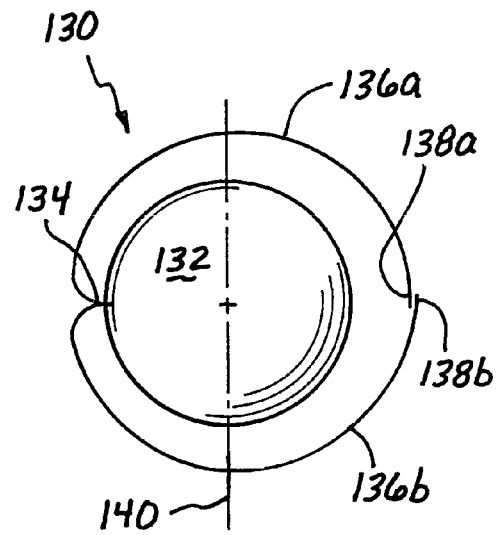
FIG. 10 is a schematic plan view of the alternative intraocular lens of the present invention having a single fixation member that diverges into two outer ends.

An example of a single fixation member IOL 130 with multiple strands is seen in FIG. 10. A fixation member has an inner end 134 that connects to an optic 132. The fixation member splits into two accommodating beams 136a, 136b that extend approximately halfway around the circumference of the optic 132 to terminate at free ends 138, 138b. In this regard, the beams 136a, 136b are each longer than previous fixation members and thus permit greater accommodation movement of the optic 132. A meridian plane 140 again divides the IOL 130 into leading (left) and trailing (right) halves such that the IOL 130 inserts to the left and the free ends 138a, 138b of the beams 136a, 136b are on the trailing end.

For human implantation, the exemplary IOLs disclosed herein may be configured such that the amount of positive or near accommodation is preferably at least about 1 diopter and may range up to 3.5 diopters or more. Further, IOLs may be configured to provide at least about 2.0 mm of posterior axial movement in the eye with a reduction of about 2.0 mm in the equatorial diameter of the capsular bag 22 caused by the ciliary muscle 34 and the zonules 36.

The optics may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through a small incision into the eye. Although the optic as shown is a refractive lens body, the present IOLs may include a diffractive lens body, and such embodiment is included within the scope of the present invention.

With reference to the first embodiment of FIGS. 3-5, but also applicable to the other embodiment, the optic 24 is desirably integrally formed with the movement assembly 26 (i.e., fixation members 50a, 50b). That is, the fixation members 50a, 50b are formed of the same homogeneous biocompatible material as the optic 24, preferably polymeric materials such as polypropylene, silicone polymeric materials, acrylic polymeric materials, and the like. The movement assembly 26 is preferably deformable in much the same manner as the optic 24 to facilitate the passage of the IOL 20 through a small incision into the eye. The material or materials of construction from which the movement assembly 26 is made are chosen to provide the assembly with the desired mechanical properties, e.g., strength and deformability, to meet the needs of the particular application involved.

The IOL 20 may be inserted into the capsular bag 22 of a mammalian eye using conventional equipment and techniques, for example, after the natural crystalline lens is removed, using a phacoemulsification technique. The IOL 20 is preferably rolled or folded prior to insertion into the eye to be insertable through a small incision, for example, on the order of about 3.2 mm. After insertion, the IOL 20 may be positioned in the eye as shown in FIG. 1.

If the IOL 20 is to be implanted in an adult human eye, the optic 24 preferably has a diameter in the range of about 3.5 mm to about 7 mm and, more preferably, in the range of about 5 mm to about 6 mm. Further, the IOL 20 may have an overall diameter, with the movement assembly 26 in an unstressed condition, of about 8 mm to about 11 mm or 12 mm. Additionally, the optic 24 preferably has a far-vision correction power for infinity in an un-accommodated state.

While the present invention has been described with respect to various specific examples and embodiments, it is to be understood that the invention is not limited thereto and that it can be variously practiced within the scope of the following claims.

What is claimed is:

1. An intraocular lens, comprising:
   an optic configured for implantation in the capsular bag of an eye comprising a circular periphery centered about an optical axis;
   an optic plane passing through the center of the optic and perpendicular to the optical axis;
   a fixation member configured to convert radial movement of the capsular bag to axial movement of the optic and to provide accommodating movement of at least about 1 diopter, the fixation member comprising an elongate stabilizing arm and an elongate accommodating beam that is substantially straight along its length, the elongate accommodating beam operably connected to the elongate stabilizing arm, the elongate stabilizing arm having a free end; and
   a transition section having an inner portion connected to the optic periphery and an outer portion connected to an inner end of the elongate accommodating beam, the outer portion being displaced along the optical axis with respect to the inner portion;
   wherein the fixation member extends generally in a plane parallel to the optic plane but displaced therefrom, the elongate stabilizing arm and the elongate accommodating beam form an obtuse angle;
   wherein the accommodating beam is wider in plan view than the stabilizing arm.

2. An intraocular lens, comprising:
   an optic configured for implantation in the capsular bag of an eye comprising a circular periphery centered about an optical axis and a diameter;
   an optic plane passing through the center of the optic and perpendicular to the optical axis;
   a fixation member configured to convert radial movement of the capsular bag to axial movement of the optic and to provide positive accommodating movement of at least about 1 diopter, the fixation member comprising an elongate accommodating beam having a length that is greater than the diameter of the optic, the elongate accommodation beam being substantially straight along the length thereof and
   a transition section having an inner portion connected to the optic periphery and an outer portion connected to an inner end of the elongate accommodating beam, the outer portion being displaced along the optical axis with respect to the inner portion; and
   a stabilizing arm connected to the accommodating beam, wherein the accommodating beam is wider in plan view than the stabilizing arm.

3. The intraocular lens of claim 2, further a living hinge disposed between the accommodating beam and the stabilizing arm, the living hinge being thinner in a plan view than stabilizing arm.

4. An intraocular lens, comprising:
   an optic configured for implantation in the capsular bag of an eye comprising a circular periphery centered about an optical axis and an optic plane passing through the center of the optic and perpendicular to the optical axis;

a fixation member configured to convert radial movement of the capsular bag to axial movement of the optic and to provide positive accommodating movement of at least about 1 diopter, the fixation member comprising an elongate accommodating beam that is substantially straight along the length thereof, the elongate accommodating beam having a length that is greater than a diameter of the optic; and a transition section having an inner portion with a circumferential midpoint and an outer portion connected to an inner end of the elongate accommodating beam, the inner portion being connected to the optic periphery, the outer portion being displaced along the optical axis with respect to the inner portion;

wherein the fixation member extends generally in a plane parallel to the optic plane but displaced therefrom;

wherein a line disposed through the optical axis and the circumferential midpoint forms an acute angle with a line disposed along the length of elongate accommodation beam; and a stabilizing arm, the elongate accommodating beam being substantially wider in plan view than the stabilizing arm and connected thereto at a relatively thin living hinge.

* * * * *